(12) United States Patent
Parienti

(10) Patent No.: US 6,560,482 B1
(45) Date of Patent: May 6, 2003

(54) SYSTEM FOR APPLYING GOLD TO THE FACE SKIN TISSUES

(76) Inventor: Raoul Parienti, 5 Rue do Belgijue 06000, Nice (FR)

( * ) Notice: Subject to any disclaimer, the term of this patent is extended or adjusted under 35 U.S.C. 154(b) by 0 days.

(21) Appl. No.: 09/424,992

(22) PCT Filed: Apr. 8, 1998

(86) PCT No.: PCT/FR98/00706

§ 371 (c)(1),
(2), (4) Date: Dec. 3, 1999

(87) PCT Pub. No.: WO98/46302

PCT Pub. Date: Oct. 22, 1998

(51) Int. Cl.$^7$ .................. A61N 1/30; A61H 33/04
(52) U.S. Cl. ............................ 604/20; 604/303
(58) Field of Search ............... 604/20, 19, 65, 604/66, 289, 290, 292, 293, 303; 606/41, 42; 607/50

(56) References Cited

U.S. PATENT DOCUMENTS

| | | | |
|---|---|---|---|
| 4,317,457 A | 3/1982 | Guillot | 128/783 |
| 4,391,270 A * | 7/1983 | Uragami | 600/15 |
| 4,405,311 A | 9/1983 | Greatbatch | 604/20 |
| 4,411,648 A | 10/1983 | Davis | 604/21 |
| 4,895,154 A * | 1/1990 | Bartelt et al. | 607/50 |
| 5,443,441 A | 8/1995 | De Claviere | 604/20 |
| 5,587,168 A * | 12/1996 | Vanonou | 424/401 |
| 5,733,259 A * | 3/1998 | Valcke et al. | 128/DIG. 12 |

FOREIGN PATENT DOCUMENTS

| | | |
|---|---|---|
| DE | 28 28 936 | 1/1980 |
| EP | 0 547 482 | 6/1993 |
| EP | 0 778 046 | 6/1997 |
| FR | 2336949 | 7/1977 |
| FR | 2661616 | 11/1991 |

* cited by examiner

Primary Examiner—Michael J. Hayes
(74) Attorney, Agent, or Firm—James C. Lydon

(57) ABSTRACT

The invention concerns a method for applying gold to patient's face skin tissues comprising a device generating a unipolar voltage, a mask whereof the internal wall is covered with gold and designed to be placed on the patient's face by means of a gel-type fluid acting as electrolyte in contact with the internal wall, the mask being connected to the voltage generating device positive terminal, and a patient's electrode in contact with the patient's body cutaneous part and connected to the voltage generating device negative terminal such that the gold atoms are transferred from the mask to the patient's skin by electrolysis through the fluid.

10 Claims, 1 Drawing Sheet

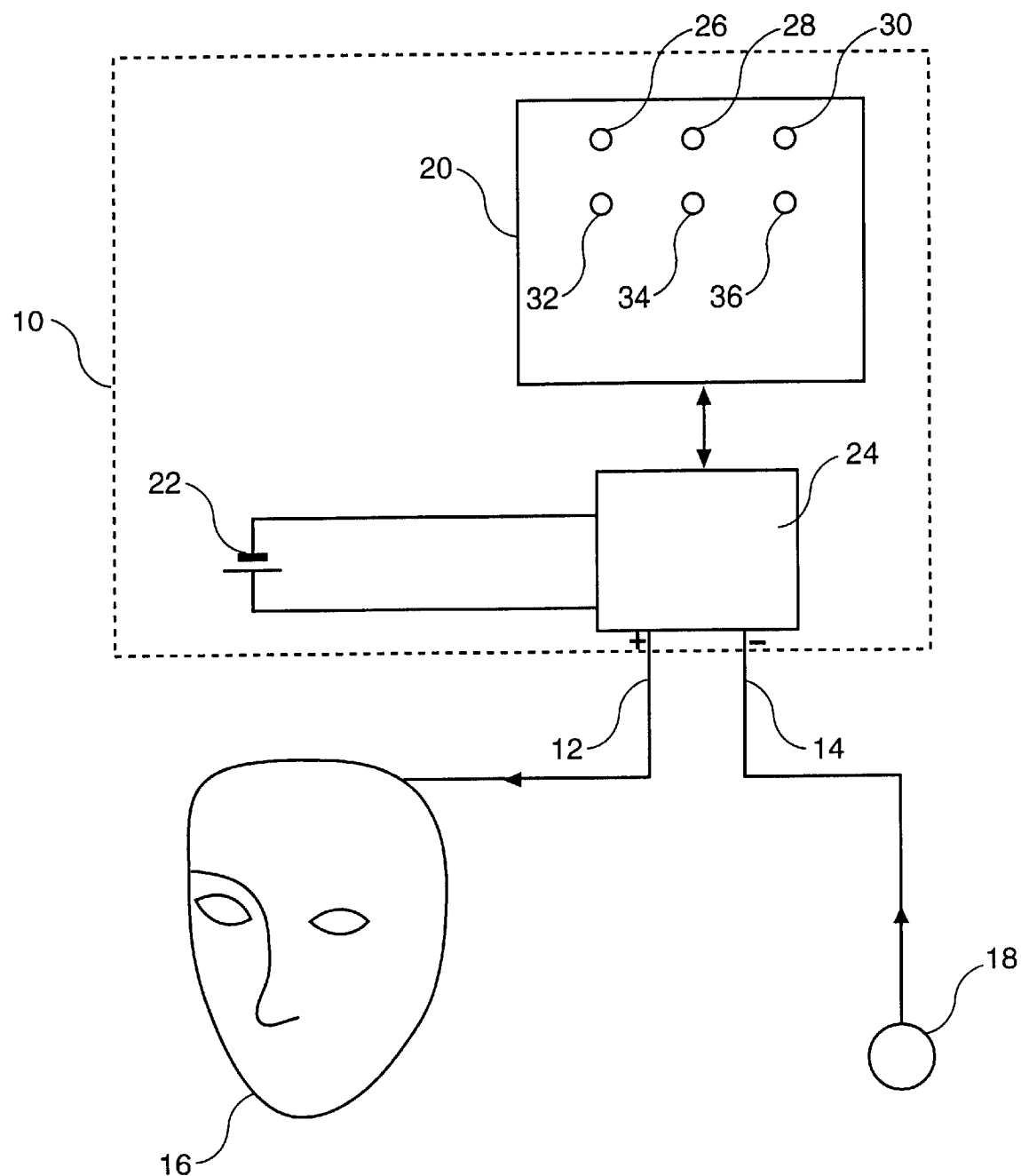

SYSTEM FOR APPLYING GOLD TO THE FACE SKIN TISSUES

TECHNICAL FIELD

This invention relates to a system for applying gold atoms onto the face with the aim of remodelling the tissues in order to remove small wrinkles from the face.

PRIOR ART

The beneficial therapeutical uses of gold have been known since time immemorial. Moreover, for more than a decade, the pharmacopoeia has made increasing usage of the tonic, bactericidal, and regenerative virtues of gold administered orally or placed under the tongue.

Over the last twenty years or so, traditional Chinese techniques such as acupuncture have become increasingly popular in the West, and have shown that very thin gold needles inserted into small wrinkles caused them to noticeably reduce in size and had a remodelling action on adjacent tissues, providing the face with a long lasting healthy appearance. However, the method of application is not homogenous and is not suitable for individuals who cannot cope with needles being introduced into their skin.

SUMMARY OF INVENTION

The object of the invention is thus mainly to provide a system for applying gold atoms in an homogeneous manner onto the skin of the face with no need for introducing needles.

The invention thus concerns a system for applying gold to a patient's facial skin tissues, comprising a device generating a single-pole voltage, a mask whereof the internal surface is covered with gold and designed to be placed on the patient's face by means of a gel-type fluid which acts as an electrolyte in contact, on the one hand, with the face skin and on the other hand with the mask internal surface, the mask being connected to the positive terminal of a voltage generating device, and a patient's electrode in contact with the cutaneous part of the patient's body and connected to the negative terminal of the voltage generating device such that the gold atoms are transferred from the mask to the patient's skin by electrolysis through the fluid.

BRIEF DESCRIPTION OF THE DRAWING

The sole FIGURE is a schematic illustration of a system for applying gold to a patient's facial skin tissues.

DESCRIPTION OF THE INVENTION

The objects and features of the invention will become more apparent from the following detailed description with reference to the single FIGURE enclosed herewith.

A system according to the invention comprises substantially a control box 10 as a single-pole voltage generating device, shown as the dotted line on the figure and having two output terminals, one positive terminal 12 connected to a mask 16 acting as an anode and a negative terminal 18 acting as a cathode.

The control box 10 comprises a control unit 20 such as a microprocessor, a power supply source 22 providing a low voltage output, preferably ranging from 3 to 6 volts and a voltage converter/supply 24 designed to provide a specific voltage at the output terminals 12 and 14.

The mask 16 is preferably made of a flexible material such as a polymer, charged with carbon powder or any other powder material capable of making it conductive. Its internal surface is covered with a thin layer of gold, for example 1 or 2 micrometers thick, obtained by electrolysis or by any other gilding process. The main thing is to have a tight contact between the mask's flexible material and the gold layer so that a good connection is ensured with the positive terminal.

Before applying the mask, the patient's face is smeared with a gel or any other fluid used as an electrolyte. The latter contains a mix of acids (for example nitric and sulphuric acids) containing gold ions in solution. The acids must be diluted so as not to damage the skin, a dilution providing a pH of 4 or 5 being adequate for obtaining a good electrolyte.

The electrolyte could be any solution containing gold ions such as seawater for example. While seawater already contains gold in the form of ions (4 mg/m$^3$), gold atoms must be added to it.

Using a gel is better than using any other fluid because a gel, such as a silicone or an acrylic gel, can adapt itself to the face's shape when the mask 16 is applied.

The negative terminal 14 is connected to the cathode 18 which takes preferably the form of a conductive bracelet attached around one of the patient's wrists.

As shown in the figure, the microprocessor 20 connected to the voltage converter/supply 24 features several controls 26 through 36 for adjusting the various system control settings. In this manner, control 26 controls how long the system is applied (for example from 15 min. to 30 min., control 28 controls the amount of voltage applied between terminals 12 and 14, and control 30 controls the shape or the modulation of the voltage applied. The other controls could concern the patient. Hence, control 32 may indicate the patient's age as the voltage to be applied is based on age, control 34 may indicate the patient's sex as the voltage to be applied depends on whether the patient is male or female, and control 36 may be used to indicate skin condition (dry, wet, greasy, . . . ).

Generally speaking, the microprocessor may have as many commands as necessary and also a LCD screen for displaying, for example, the voltage applied.

In order to improve the application of gold onto the skin, the voltage level between the two output terminals 12 and 14 may vary within the same polarity. In this manner, this voltage may take the form of positive pulses such as square waves or a sequence of sine half-waves of a rectified alternating current voltage.

Applying a voltage for a period of about 20 min enables a few micrograms of gold to be applied on the subcutaneous part of the face. In order to clean out skin pores that might be blocked after the current has been applied, it is a good idea to reverse the current polarity for a short period before the application is finished. When the operation is finished, and if the mask's gold layer thickness was set properly, no gold should remain on the mask which then recovers its original appearance.

What is claimed is:

1. A system for applying gold to facial skin tissues comprising:
   a single-pole voltage generating device,
   a mask, the internal surface of which is covered with gold, said mask being capable of being placed on a patient's face using an electrolyte in contact with said internal mask surface, said mask adapted to be connected to a positive terminal of said voltage generating device, and
   a patient's electrode adapted to be in contact with a cutaneous part of the patient's body and adapted to be connected to a negative terminal of said voltage generating device;

such that in operation gold atoms are transferred from said mask to a patient's skin by electrolysis.

2. The system according to claim 1, wherein said single-pole voltage generating device comprises:

a power supply source capable of delivering a continuous voltage, a voltage converter/supply provided with a positive output terminal adapted to be connected to said mask and a negative output terminal adapted to be connected to said patient's electrode, for supplying said single-pole voltage, and a microprocessor connected to said voltage converter/supply for controlling settings that determine said single-pole voltage.

3. The system according to claim 2, wherein said microprocessor has several control buttons including a control button for setting a duration of the application, a control button for setting a voltage value applied and a control button for setting a shape of the voltage applied.

4. The system according to claim 3, wherein said microprocessor further includes a control button for setting the patient's age, a control button for setting the patient's sex, and a control button for setting the condition of the patient's facial skin.

5. The system according to claim 1, wherein a value of said single-pole voltage provided by a converter/supply ranges from 3 to 6 Volts.

6. The system according to claim 1, wherein a value of said single-pole voltage provided by a converter/supply has a form of positive pulses.

7. The system according to claim 1, wherein a value of said single-pole voltage provided by a converter/supply is reversed for a short period at the end of normal application duration.

8. The system according to claim 1, further comprising an electrolyte suitable for application onto the face of said patient prior to placement of said mask.

9. The system according to claim 8, wherein said electrolyte comprises gold ions in solution.

10. The system according to claim 8, wherein said electrolyte is a gel.

* * * * *